US00PP07812P

United States Patent [19]

McKenzie, deceased et al.

[11] Patent Number: Plant 7,812

[45] Date of Patent: Mar. 3, 1992

[54] APPLE TREE NAMED 'SCIEUR'

[76] Inventors: Don McKenzie, deceased, late of Havelock North; by Joy McKenzie, personal representative, P.O. Box 8345, Havelock North; Allan G. White, R.D. 2, Hastings, all of New Zealand

[21] Appl. No.: 566,282

[22] Filed: Aug. 13, 1990

[51] Int. Cl.[5] ..... A01H 5/00
[52] U.S. Cl. ..... Plt./34
[58] Field of Search ..... Plt./34

[56] References Cited

U.S. PATENT DOCUMENTS

P.P. 2,460 12/1964 Roberts ..... Plt. 34
P.P. 3,637 10/1974 McKenzie ..... Plt. 34

*Primary Examiner*—James R. Feyrer
*Attorney, Agent, or Firm*—Quarles & Brady

[57] ABSTRACT

The new and distinct variety is a selection from a population of open pollinated seedlings of the apple variety Splendour (U.S. Plant Pat. No. 2,460). The fruit of the apple tree of this variety has an attractive appearance characterized by its striped color pattern. The new variety has been named "Scieur".

1 Drawing Sheet

SUMMARY OF THE INVENTION

The new variety was selected from a population of open pollinated seedlings of the apple variety Splendour (U.S. Plant Pat. No. 2,460) in 1984. The new variety was distinguishable from Splendour as well as Gala (U.S. Plant Pat. No. 3,637) and Sciray, Sciros and Sciglo (the subject of co-pending applications filed on even date herewith by the same applicants). The features which distinguish the new variety from the aforementioned varieties are:

Gala: Flat shape, acid flavour, later season.
Splendour: Flat shape, acid flavour, earlier season, striped colour pattern.
Sciray: Flat shape, acid flavour, red-orange striped colour pattern, later season.
Sciros: Flat shape, acid flavour, red-orange striped colour pattern, earlier season, softer flesh.
Sciglo: Later maturity, red-orange striped colour pattern, flat shaped, acid flavour.

The new variety has been named "Scieur" variety. Asexual propagation by budding shows that the unique combination of characteristics and distinctive colour come true to form and are established and transmitted through succeeding propagations.

BRIEF DESCRIPTION OF THE DRAWINGS

The accompanying drawings show typical specimens of the foliage and fruit of the new variety as depicted in colours as nearly true as is reasonably possible to make the same in a colour illustration of this character.

View A is a side view of an apple of the variety.

View B is a bottom view of an apple of the variety.

View C is a cross sectional view of an apple of the variety.

View D is a top view of an apple of the variety.

Figure 1:
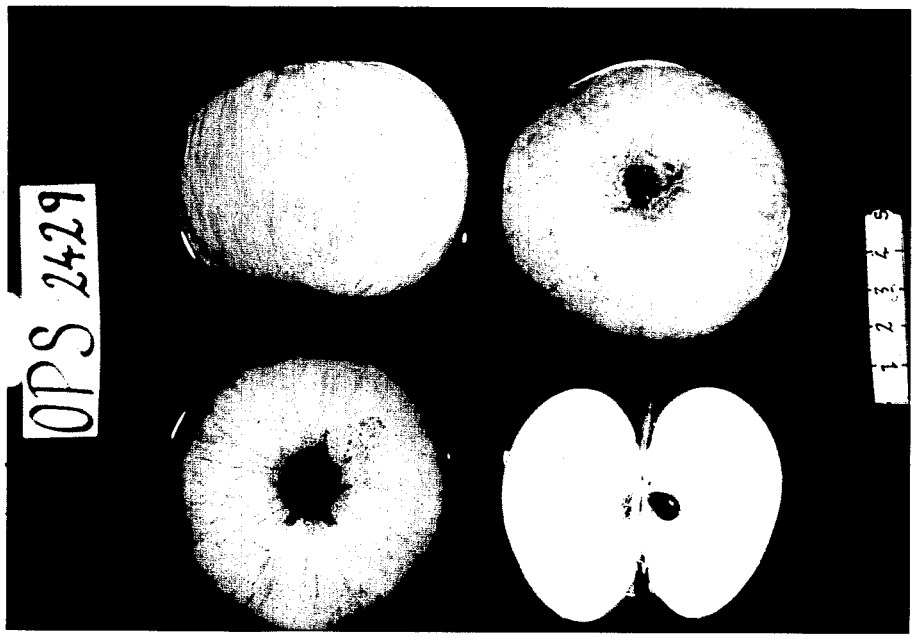
FIG. 1 is a close up view of the four apples of the variety. Beginning in the upper right corner and proceeding clockwise.
Figure 2:
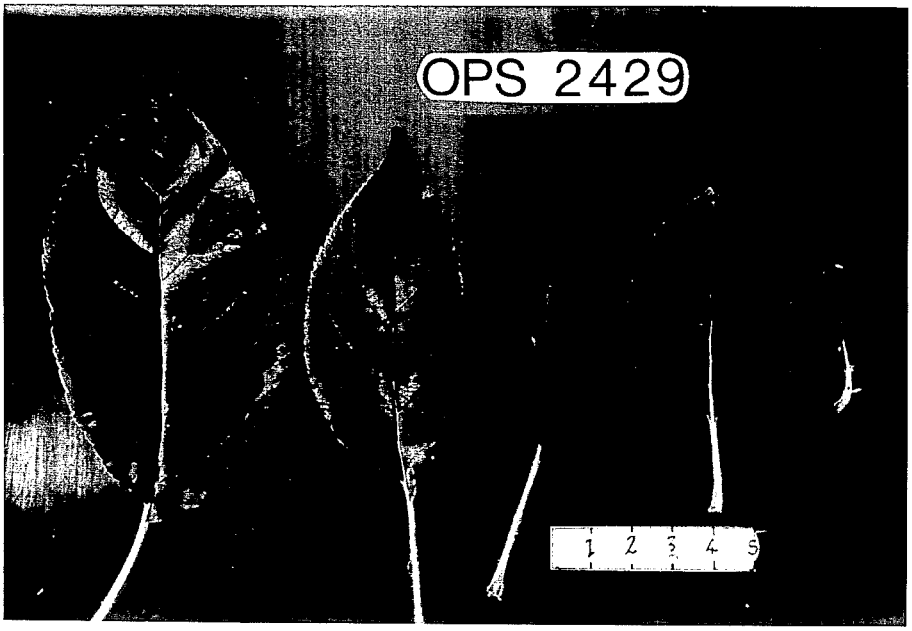

FIG. 2 is a view showing five leaves of the variety.

DETAILED DESCRIPTION OF THE DISCLOSURE

The following is a detailed description of the new variety with color terminology in accordance with the Royal Horticultural Society Colour Chart (R.H.S.C.C.) except where general color terms of ordinary meaning are used as is clear from the context.

The specimens described were grown at Havelock North, New Zealand. The observations were made in the 1989 season on trees which were three years old at the time.

The fruit ripened for eating towards mid-season. Specifically harvest commences about March 14 and ends about April 1 in New Zealand. Blossom commences about October 12 and full bloom occurs by October 24 in New Zealand.

Tree: Medium-small; upright habit; bearing, in spurs; vigor medium with annual growth for eight year old trees with MM106 rootstock being about 250 mm; spurs occurring at a rate of 3.5 per 10 cm. on three year old growth.

Trunk: Medium size, moderately rough, the bark is RHSCC 200D when new and RHSCC 165B when old.

Branches: Medium thickness, moderately rough, medium branching; the angle of branching being commonly 15 degrees above the horizontal; the spread-to-height ratio being about 1 to 3.

Lenticels: Average; small.

Leaves:

*Length.*—4 11/16 inches.

*Width.*—2½ inches; medium size; outward pose; medium length/width ratio of blades; concave to straight shape in cross-section; serrate indentation of margin; medium glossiness of upper side; medium pubescence on lower side; long petiole length; medium stipule size; medium time of bud burst; the color of the blade is RHCSS 137B, the stems are RHSCC 156B and 179B, and the veins are RHSCC 157A.

Flowers: Medium time of beginning of flowering (10% flowers); medium size; flat shape; margin of petals, overlapping; colour of bud just before flower opens, pink.

Fruit: Examined at peak maturity.

*Soluble solids.*—14.5.

*Size.*—Large; axial diameter, 2 5/16 inches; transverse diameter 2 15/16 inches.

*Shape.*—Uniform; medium to long cylindrical; symmetrical in side view; ribbing present; weak crowning at distal end.

*Cavity.*—Medium depth; medium width.

*Basin.*—Shallow to medium depth; medium to broad width; ribbing present.

*Stem.*—Medium thickness (comparable to Cox's Orange Pippin); long length (comparable to Red Delicious).

*Calyx.*—Closed; calyx tube length, medium; calyx tube width, medium; calyx tube shape, U or V shaped.

*Sepal.*—Length, medium; spacing, free.

*Eye.*—Size, medium; aperture, open.

*Skin.*—Medium thickness; smooth; bloom of skin, absent; greasiness of skin, present; cracking tendency of skin, absent; background colour, orange-yellow/green RHSCC 10B.

*Over-colour.*—Approximately fifty percent of over-colour of skin; red RHSCC 45A; striped; weak russet about stem cavity.

*Flesh.*—Juicy; soft; cream; crisp-tender, melting; Penetrometer equals 5.6 kg.; medium browing of flesh (one hour after cutting, stainless steel blade).

*Texture.*—Medium.

*Flavour.*—Strong sweetness; medium acidity (pH about 3.6); acid-sugar balanced; similar acid to Cox's Orange Pippin, less aromatic than Cox's Orange Pippin.

*Weight of fruit.*—180 gm.

*Quality.*—Excellent.

*Core.*—Distinctness of core line in cross-section (median through locules), weak to medium; aperture of locules in cross-section, open; central cavity (in cross-section), absent.

*Sinus.*—Closed.

*Seeds.*—Five locules; 8 to 10 seeds total, 2 seeds per locule maximum; seed length 9 mm.; seed width 5 mm.; form obtuse; color RHSCC 165A.

Use: Market, dessert.

Keeping quality: Very good; no disorders after 98 days.

Resistance to:

*Insects.*—Good.

*Diseases.*—Good.

Production: Early and regular cropping; tendency to biennial bearing if overcropped.

Growth habit: Standard, fruit bourne on short spurs.

Management: Trees require pruning in winter and fruit thinning in early summer. Trees in test plot trained as center leader trees. Natural habit is an open textured tree with few strong upright branches.

It is claimed:

1. A new and distinct variety of apple tree which is a selection from a population of open pollinated seedlings of the Splendour variety (U.S. Plant Pat. No. 2,460) substantially as shown and described characterized by its striped colour pattern and sweet flavour.

* * * * *